United States Patent [19]
Yaskoff et al.

[11] Patent Number: 5,997,813
[45] Date of Patent: Dec. 7, 1999

[54] CONDENSATE TEMPERING SYSTEM FOR USE WITH STEAM STERILIZERS

[75] Inventors: Francis X. Yaskoff, Westborough; Kevin E. Sullivan, Brighton; Alfred B. Scaramelli, Bedford, all of Mass.

[73] Assignee: Commonwealth H2O Matrix, Boston, Mass.

[21] Appl. No.: 09/020,586

[22] Filed: Feb. 2, 1998

Related U.S. Application Data

[60] Provisional application No. 60/062,520, Oct. 17, 1997.

[51] Int. Cl.$^6$ ........................................................ A61L 2/08
[52] U.S. Cl. ............................ 422/26; 422/108; 422/109; 422/110; 422/295; 422/297
[58] Field of Search .............................. 422/26, 108–110, 422/255, 260, 295, 297

[56] References Cited

U.S. PATENT DOCUMENTS

| | | | |
|---|---|---|---|
| 4,238,447 | 12/1980 | Wolff | 422/26 |
| 4,808,377 | 2/1989 | Childers et al. | 422/26 |
| 4,944,919 | 7/1990 | Powell | 422/26 |
| 5,026,524 | 6/1991 | Powell et al. | 422/26 |
| 5,480,610 | 1/1996 | Birkholz et al. | 422/26 |
| 5,527,516 | 6/1996 | Yamamoto et al. | 422/292 |

*Primary Examiner*—Krisanne Thornton
*Attorney, Agent, or Firm*—Hale and Dorr LLP

[57] ABSTRACT

A steam condensate tempering system for a steam sterilizer uses a fast temperature sensor to measure the temperature of combined water and steam condensate from a sterilizer, and a controller for controlling the flow of cool water to mix with the steam condensate in response to the temperature sensed by the temperature sensor.

15 Claims, 2 Drawing Sheets

CONDENSATE TEMPERING SYSTEM FOR USE WITH STEAM STERILIZERS

CROSS-REFERENCE TO RELATED APPLICATION

This application claims the benefit of U.S. Provisional Application No. 60/062,520 filed Oct. 17, 1997, which is expressly incorporated herein by reference for all purposes.

BACKGROUND OF THE INVENTION

In steam sterilizers used in hospitals, universities, and other facilities in which it is necessary to sterilize equipment, steam can be used to perform the sterilization. One type of steam-based sterilizer has a sterilization chamber into which the components are put, and an outer jacket around the chamber for warming and insulating the sterilization chamber. Steam is introduced into the jacket to insulate and heat the chamber, and separately into the chamber to sterilize the components. The steam from the jacket and chamber is collected in steam traps that provide steam condensate toward a drain.

Building codes typically specify that water provided from equipment to a drain not be hotter than a certain temperature, such as 140° F., to minimize damage to the pipes and leaching of heavy metals. Consequently, the steam condensate must be cooled before it is provided down the drain. In typical sterilizers currently in use, the steam condensate provided from the steam traps is mixed with cooling water from a cool water line, typically a municipal water line. The combined cooling water and steam condensate is provided to a funnel that has an air gap to prevent drain water from mixing into lines in the sterilizer. The combined water is then provided down the drain.

The cool water line is typically connected to provide cooling water continuously at a rate of 0.5 to 5 gallons per minute, depending on the particular sterilizer system. Furthermore, there is typically a separate municipal water line serving the jacket and the chamber steam condensate lines. Such a cooling system thus causes a very large amount of cool water to be provided down the drain, even if much of that cool water is excessive for meeting building code requirements.

SUMMARY OF THE INVENTION

The present invention includes a steam condensate tempering system for use with steam sterilizers and methods for controlling cooling water flow in connection with sterilizing components. The systems and methods herein substantially reduce the consumption of water compared to typical steam sterilizers currently in use. The system is particularly adapted, but not necessarily limited, to sterilizers that have a sterilizing chamber and an outer jacket, both of which receive steam over separate lines and provide steam condensate via separate steam traps.

The present invention includes a method for retrofitting a steam sterilizer to provide significant water savings while not interfering with the sterilization process, and without effecting any change to the operation of the sterilizer itself. The method is used with a sterilizer that has at least a sterilizing chamber and typically a funnel that receives steam condensate from the chamber (via a steam trap) mixed with cooling water from a relatively cool water line, such as a municipal water line (or a private water line). The method includes providing a controllable valve in the cool water line, coupling the cool water line in the system so that cooling water mixes with the steam condensate from the chamber, providing a temperature sensor to monitor the temperature of the water to be provided to the drain, and providing a controller that is responsive to the sensed temperature to control the valve based on a relationship between the sensed temperature and a threshold temperature.

According to another aspect, the present invention includes a system for cooling steam condensate from a steam sterilizer. The system has a valve in a relatively cool water line for controlling the flow of cooling water. A temperature sensor is provided in the drain line, and preferably in a mixing chamber that receives steam condensate and cooling water, to quickly sense the temperature of the water in the mixing chamber. A controller receives signals from the temperature sensor and controls the valve in response thereto. If the sensed temperature exceeds a threshold level, such as 120° F., the controller actuates the valve so that more cooling water can be provided. If the temperature of the water in the mixing chamber is less than the threshold level, the valve for the cooling water is kept off.

While sterilizers have been used for many years with a continuously running cool water line to cool the steam condensate provided to the drain, the present invention provides substantial savings in terms of water supply and consequently in cost to the institution with the sterilizer(s) while keeping the water sufficiently cool to meet the requirements of building codes. It has been found that the water savings for cooling the steam condensate from the chamber and jacket can be up to 90% with the system of the present invention compared to prior sterilizer designs. This efficiency represents a savings of about 500,000 gallons of water on average per sterilizer per year, which can be over 20,000,000 gallons of water per year in a single medical/research facility. In addition, the design according to the present invention allows changes to be made to an existing sterilizer without affecting the operation of the sterilizer or the sterilization process. Other features and advantages will become apparent from the following detailed description, drawings, and claims.

DETAILED DESCRIPTION

Figure 1:
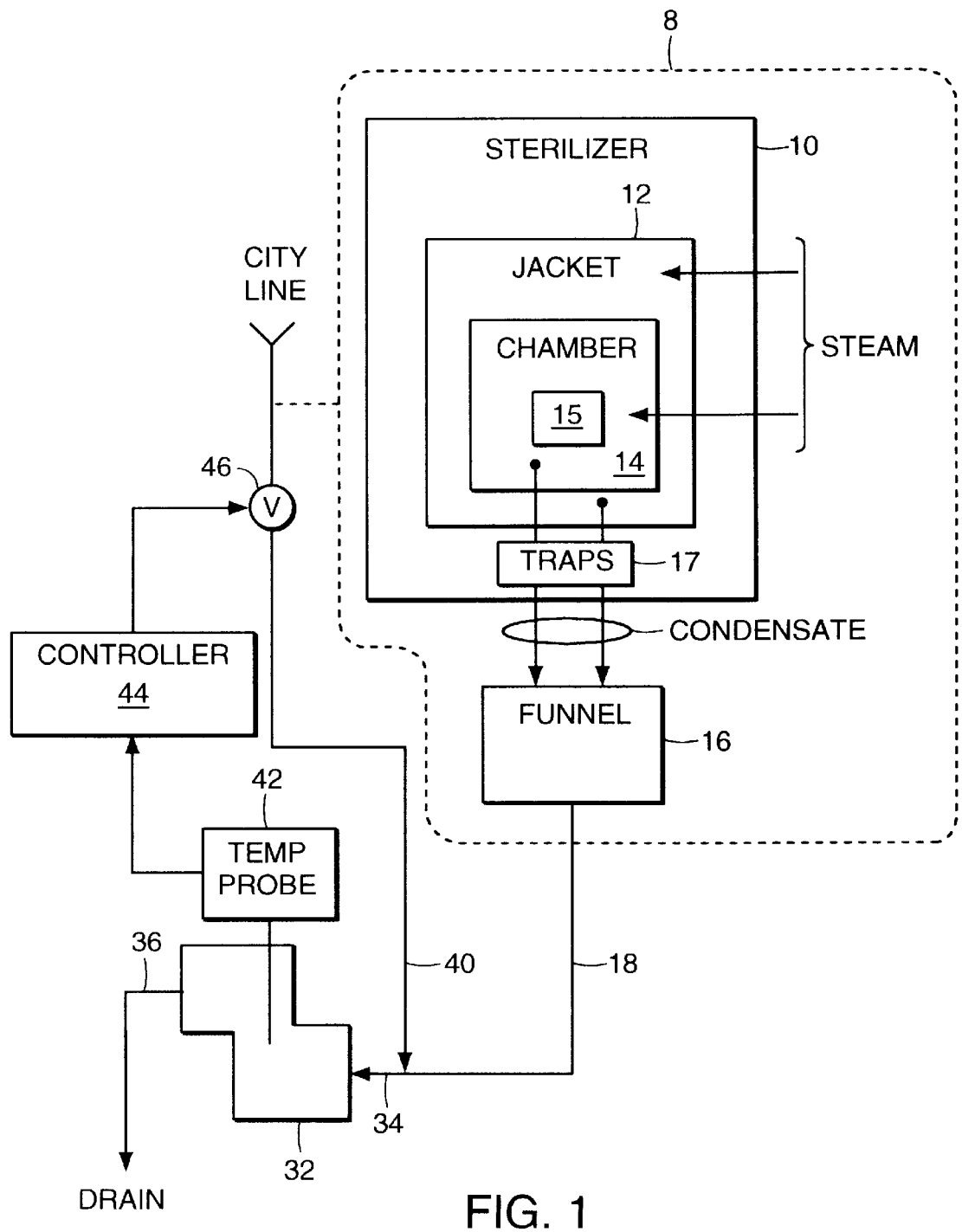
FIG. 1 is a schematic block diagram of a sterilizer according to the present invention.

Referring to FIG. 1, a sterilizing system 8 has a sterilizer 10 with a chamber 14 surrounded by a jacket 12. Steam is introduced into chamber 14 to sterilize components 15, and into jacket 12 to insulate chamber 14. Jacket 12 is also used to heat chamber 14 during a drying cycle after sterilization. Steam condensate is provided from both chamber 14 and jacket 12 to a funnel 16 via separate steam traps 17, and thereafter to a drain line 18. Funnel 16 provides an air gap to prevent water in drain line 18 from mixing with lines in sterilizer 10.

In prior systems, cool water would be continuously injected from a municipal water line to mix with the steam condensate before it reaches funnel 16. Funnel 16 would thus receive a mixture of steam condensate and relatively cool water. For convenience, in such prior systems (many of which are currently in operation), the cool water line was connected such that it provided cooling water continuously, 24 hours a day, at a rate of 0.5 to 5 gallons per minute (GPM), depending on the system. Typically, there would be a separate cool water line for the jacket and the chamber. An example of such a sterilizer is an AMSCO Eagle series sterilizer, which is available from Steris Corporation, located in Mentor, Ohio.

The condensate tempering system of the present invention provides substantial water savings by replacing the continuous flow of the cool water line with a controllable system. The system includes a mixing chamber 32 with an inlet 34 at a lower portion of mixing chamber 32, and an outlet 36 at an upper portion of mixing chamber 32. Inlet 34 is connected to drain line 18 from funnel 16, and is also in fluid communication with a relatively cool water line 40, typically from a municipal water supply.

A fast response temperature probe 42, i.e., a temperature probe that can sense temperature in a short period of time (preferably in several seconds), is provided in mixing chamber 32 and provides to a controller 44 signals indicating the temperature of the water in mixing chamber 32. Controller 44 compares the sensed temperature to a chosen threshold, such as 120° F. If the temperature exceeds the threshold, the controller causes a valve 46, such as a solenoid valve, to open so that cooling water flows in line 40 to mixing chamber 32. The cooling water mixes with the steam condensate from funnel 16. Mixing chamber 32 also allows for some mixing before the resulting mixed water is provided to the drain.

By using such a temperature probe, controller, and valve, it is not necessary to keep the cool water line running at all times. It has been found that the system of the present invention reduces the use of water by the sterilizer for cooling the steam condensate from the chamber and jacket by up to 90% while working with existing equipment.

Assuming a maximum drain temperature of 140° F., a threshold temperature of 120° F. provides a significant buffer below a maximum temperature of 140° F. Other settings, such as 130° F., could be used, although it has been found that such a higher setting, while still keeping the water safely below 140° F., does not result in significant additional savings in water.

Figure 2:
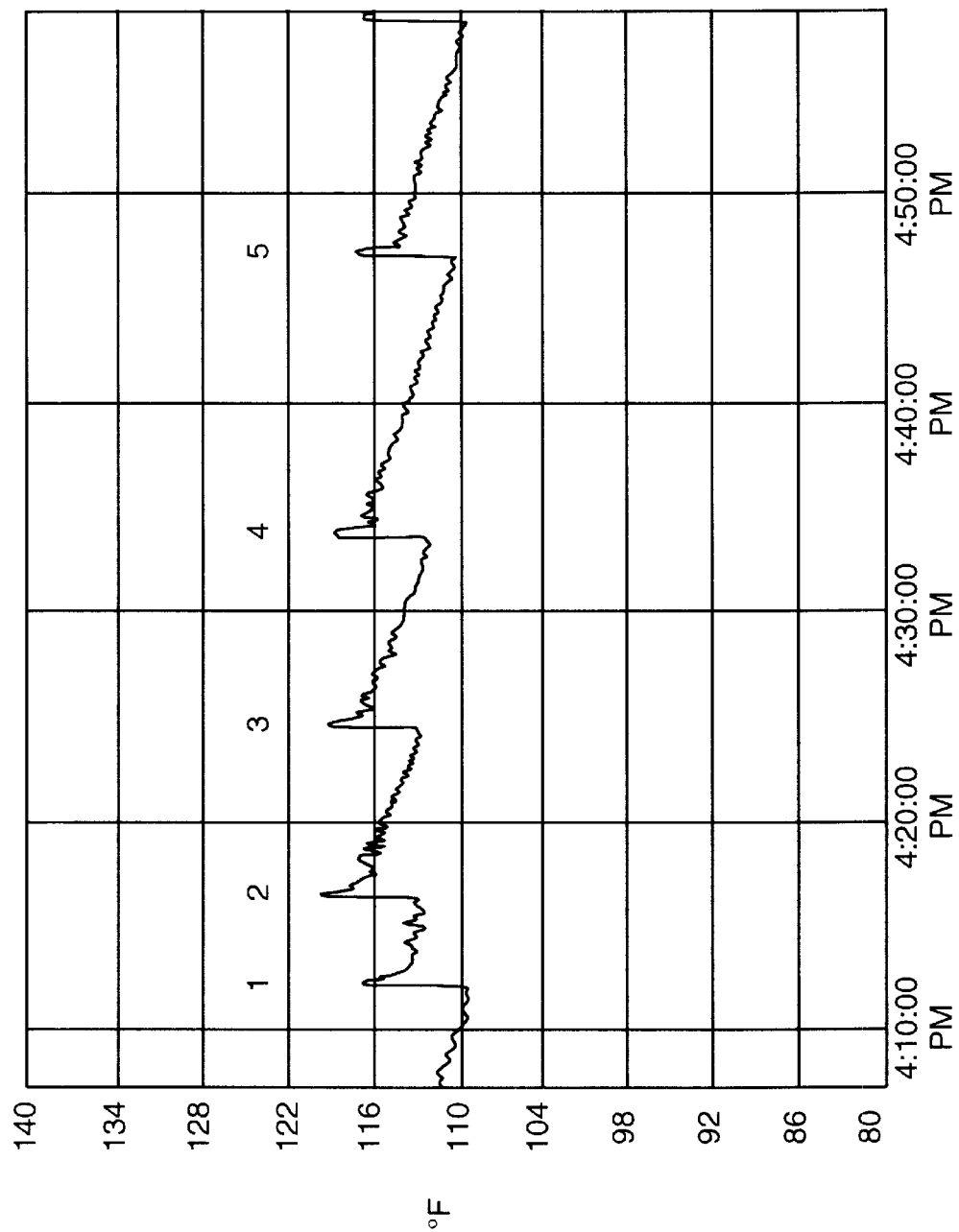
FIG. 2 is a graph illustrating the temperature of the water discharged from the steam sterilizer to the drain over time according to the present invention.

FIG. 2 shows a graph illustrating how the temperature of drain water remains below 122° F. with a system such as that described above with a controller threshold of 120° F. and a flow rate of 4 GPM. It has further been found that a desirable flow rate for the municipal water line is about 2 GPM when needed (compared to 0.5 to 5 GPM continuously in prior systems), although the flow could be still less, and savings can be realized with as low as 0.5 GPM while still sufficiently cooling the steam condensate. In FIG. 2, the temperature peaks and then declines from the five numbered peaks when the valve is opened to allow water to flow. Typically, the valve needs to be open only several seconds at a time, as the steam condensate is provided in small quantities at a time from the steam traps. For a 60-minute sterilization cycle, the total water usage can be on the order of only 2–4 gallons for cooling the steam condensate from the jacket and chamber. This water usage compares to 30–100 gallons for a typical steam sterilizer without the present invention.

Another advantage of the approach described herein is that all of the components in the tempering system can be added to the drain and provided externally without making any change to the existing sterilizer chamber, jacket, or steam traps, and therefore not affect the actual sterilization and drying processes in the chamber.

While the condensate tempering system of the present invention can be provided as part of a new sterilizer, it can also easily be retrofitted to an existing sterilizer. The present invention thus includes a method including providing a mixing chamber in the drain line, a valve in the cool water line, a temperature sensor in the mixing chamber, and a controller for controlling the valve to control the flow of water in the relatively cool water line. Note that this method of the present invention only changes the fluid flow after steam condensate is provided from the steam traps. Accordingly, the operation of the sterilizing components is not affected or altered at all.

A new sterilization system could be constructed differently from a retrofitted system as described above; for example, the mixing chamber could be eliminated and a temperature probe could be provided in some other portion of the system between the chamber and the drain, e.g., in a lower portion of a funnel with an air gap and with the cooling water provided to the funnel.

Having described an embodiment of the present invention, it should be apparent that modifications can be made without departing from the scope of the present invention. For example, the water lines could be arranged in different ways, such as coupling the cool water line directly to the mixing chamber. In any arrangement of water lines, the temperature of the steam condensate or steam condensate combined with cooling water should be sensed before the drain, and cool water should be fluidly coupled to combine with the steam condensate to reduce the temperature below a desired threshold before the water is provided down a drain. While separate traps are shown with a chamber and jacket, a single trap could be used. The temperature probe should be sufficiently fast so that there is sufficient time for the cooling water to be provided to reduce the temperature of the effluent in the lines below the desired threshold before going down the drain.

What is claimed is:

1. A steam sterilizer for sterilizing components, the sterilizer comprising:
    an insulating jacket having an inlet for receiving steam;
    a first steam trap for providing steam condensate from the jacket to a first drain line;
    a sterilizing chamber for holding components to be sterilized, the chamber being surrounded at least in part by the insulating jacket and having an inlet for receiving steam to sterilize the components,
    a second steam trap for providing steam condensate from the chamber to a second drain line;
    a cool water line fluidly coupled to provide cooling water to mix with and cool the steam condensate from the first and second steam traps;
    a mixing chamber for receiving the steam condensate from the first and second steam traps combined with the cooling water from the relatively cool water line;
    a temperature probe for sensing the temperature of the water in the mixing chamber;
    a valve for controlling the flow of the relatively cool water line; and
    a controller, responsive to the temperature probe, for controlling the valve to allow or prevent the cooling water from flowing in response to a relationship between the sensed temperature and a threshold temperature.

2. The sterilizer of claim 1, further comprising a funnel with an air gap for receiving the steam condensate from the first and second steam traps.

3. The sterilizer of claim 2, wherein the cool water line is coupled to a drain line between the funnel and the mixing chamber.

4. The sterilizer of claim 1, wherein the mixing chamber has an inlet at a lower portion of the mixing chamber and an outlet at an upper portion of the mixing chamber.

5. A method for modifying a sterilizer having a sterilizing chamber for holding components to be sterilized, the chamber having an inlet for receiving steam to sterilize the components and a drain line from which steam condensate is provided, and a funnel for receiving the steam condensate and for receiving cooling water from a cool water line in a continuous manner to cool the steam condensate from the chamber, the method comprising:

- connecting the cool water line so that cooling water mixes with the steam condensate after the steam condensate leaves the funnel;
- disabling the continuous flow of cooling water to the funnel;
- providing a temperature sensor for sensing the temperature of the mixed cooling water and steam condensate in the drain;
- providing a valve to control the flow of the cooling water; and
- operatively coupling a controller to the temperature sensor and to the valve so that the controller controls the valve based on signals received from the sensor, the controller causing the cooling water to flow or not flow depending on a relationship between the sensed temperature and a threshold temperature.

6. The method of claim 5, wherein the method is performed without changing the sterilizing chamber or affecting the process of sterilizing components.

7. The method of claim 5, further comprising providing a mixing chamber to receive combined steam condensate and cooling water, and wherein providing a temperature sensor includes providing a temperature probe in the mixing chamber.

8. The method of claim 7, further comprising coupling the cool water line to provide cooling water between the funnel and the mixing chamber.

9. A sterilizing system for sterilizing components, the sterilizing system comprising:

- a steam sterilizer with a sterilizing chamber for holding components to be sterilized, the sterilizer receiving steam and providing steam condensate at an outlet toward a drain; and
- a steam condensate tempering system coupled to the outlet of the sterilizer and including:
  - a cool water line coupled to provide cooling water to mix with and cool the steam condensate before the steam condensate reaches the drain;
  - a temperature sensor for sensing the temperature of the combined cooling water and steam condensate before the combined cooling water and steam condensate reach the drain;
  - a valve for controlling the flow of water in the cool water line; and
  - a controller, responsive to the temperature sensor, for controlling the valve so that the combined cooling water and steam condensate does not exceed a desired threshold when the combined cooling water and steam condensate reaches the drain.

10. The system of claim 9, wherein the sterilizer includes a steam trap for receiving steam from the chamber and for providing steam condensate to the tempering system.

11. The system of claim 10, wherein the steam sterilizer includes a funnel with an air gap for receiving steam condensate from the steam trap.

12. The system of claim 9, wherein the steam condensate tempering system includes a mixing chamber for receiving the combined cooling water and steam condensate, the temperature sensor sensing temperature in the mixing chamber.

13. A method for operating a steam sterilizer comprising:

- introducing steam into a sterilizing chamber of a sterilizer to sterilize components in the chamber, the sterilizer having an outlet line for providing steam condensate from the chamber toward a drain;
- providing cooling water to mix with the steam condensate:
- sensing the temperature of the combined cool water steam condensate; and
- controlling a valve to a cool water line to control the flow of cooling water based on the sensed temperature, the controlling step causing the cooling water to flow as needed to cool the water before it is provided to the drain.

14. The method of claim 13, wherein the controlling includes opening the valve when the sensed temperature exceeds a threshold.

15. A sterilizing system for sterilizing components, the sterilizing system comprising:

- a steam sterilizer with a sterilizing chamber for holding components to be sterilized, the sterilizer receiving steam and providing steam condensate at an outlet toward a drain;
- a funnel with an air gap for receiving the steam condensate and for receiving cooling water from a cool water line;
- a temperature sensor for sensing the temperature of the combined cooling water and steam condensate in the funnel;
- a valve for controlling the flow of water in the cool water line; and
- a controller, responsive to the temperature sensor, for controlling the valve so that the combined cooling water and steam condensate does not exceed a desired threshold when the combined cool water and steam condensate reaches the drain.

* * * * *